United States Patent [19]

Inoue et al.

[11] 4,101,660
[45] Jul. 18, 1978

[54] 2-AMINOMETHYL-5-PHENYLOXAZOLES AND THE PHARMACEUTICALLY ACCEPTABLE ACID ADDITION SALTS THEREOF

[75] Inventors: Sho Inoue; Katsuya Ohata, both of Kyoto; Satoshi Tsutsui, Yokohama; Tatsuo Nomura, Kawasaki, all of Japan

[73] Assignees: Mitsubishi Chemical Industries Limited, Tokyo; Nippon Shinyaku Company, Limited, Kyoto, both of Japan

[21] Appl. No.: 766,975

[22] Filed: Feb. 9, 1977

[30] Foreign Application Priority Data

Feb. 12, 1976 [JP] Japan ................................. 51-14194
Feb. 26, 1976 [JP] Japan ................................. 51-20328

[51] Int. Cl.$^2$ ................... A61K 31/495; C07D 413/06
[52] U.S. Cl. ............................... 424/250; 260/307 R; 544/369
[58] Field of Search ...................... 260/268 H, 307 R

[56] References Cited

U.S. PATENT DOCUMENTS 3,843,632  10/1974  Matsuo et al. ................... 260/307 R
4,020,082  4/1977   Marchetti ......................... 260/307 R Primary Examiner—Jose Tovar
Attorney, Agent, or Firm—Oblon, Fisher, Spivak, McClelland & Maier

[57] ABSTRACT

2-Aminomethyl-5-phenyloxazoles and the pharmaceutically acceptable salts thereof have been found to be effective for meliorating inflammation in warm blooded animals.

5 Claims, No Drawings

2-AMINOMETHYL-5-PHENYLOXAZOLES AND THE PHARMACEUTICALLY ACCEPTABLE ACID ADDITION SALTS THEREOF

BACKGROUND OF THE INVENTION

FIELD OF THE INVENTION

This invention relates to 2-aminomethyl-5-phenyloxazoles and the pharmaceutically acceptable acid addition salt thereof which exhibit anti-inflammatory and analgesic activity.

SUMMARY OF THE INVENTION

This invention relates to compounds of the formula (I):

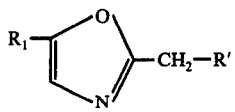 (I)

wherein $R_1$ is phenyl or halophenyl; R' is (1) 4-(2-hydroxyethyl)-1-piperazinyl or (2)

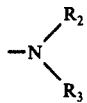

wherein $R_2$ and $R_3$ are selected from the group consisting of hydrogen and $C_1$-$C_{10}$ alkyl. Also encompassed within this invention are pharmaceutically acceptable salts thereof. This invention also relates to a method of meliorating inflammation in warm blooded animals, particularly mammals, which comprises administering to said animal an anti-inflammatory effective amount of a compound of formula (I).

DETAILED DESCRIPTION OF THE PREFERRED EMBODIMENTS

This invention relates to a group of 2-aminomethyl-5-phenyloxazoles of the formula (I):

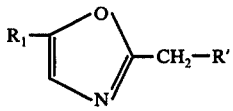 (I)

wherein $R_1$ is phenyl or halophenyl such as 2-chlorophenyl, 3-chlorophenyl, 4-chlorophenyl, 3,4-dichlorophenyl, 2-fluorophenyl, 3-fluorophenyl, 4-fluorophenyl, 2-bromophenyl, 3-bromophenyl, 4-bromophenyl, 4-iodophenyl and the like; R' is (1) 4-(2-hydroxyethyl)-1-piperazinyl or (2)

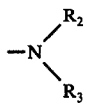

wherein $R_2$ and $R_3$ are selected from the group consisting of hydrogen and alkyl of 1–10 (preferably 1–6) carbon atoms, such as methyul, ethyl, propyl, isopropyl, butyl, isobutyl, sec-butyl, tert-butyl, isopentyl, hexyl, oxtyl, decyl and the like. Suitable $R_1$ groups in the above formula (I) are phenyl, 2-chlorophenyl, 3-chlorophenyl, 4-chlorophenyl, 3,4-dichlorophenyl, 4-fluorophenyl, 4-bromophenyl and the like.

Suitable methyl, octyl,

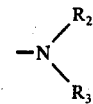

groups in the above formula (I) are amino, methylamino, ethylamino, propylamino, isopropylamino, butylamino, sec-butylamino, isubutylamino, dimethylamino, diethylamino and the like.

illustrative of the compounds of this invention are the following:
2-dimethylaminomethyl-5-(4-chlorophenyl) oxazole
2-methylaminomethyl-5-(4-chlorophenyl) oxazole
2-aminomethyl-5-(4-chlorophenyl) oxazole
2-aminomethyl-5-(4-fluorophenyl) oxazole
2-methylaminomethyl-5-phenyloxazole
2-dimethylaminomethyl-5-phenyloxazole
2-aminomethyl-5-phenyloxazole
2-ethylaminomethyl-5-phenyloxazole
2-propylaminomethyl-5-phenyloxazole
2-isopropylaminomethyl-5-phenyloxazole
2-butylaminomethyl-5-phenyloxazole
2-ethylaminomethyl-5-(4-chlorophenyl) oxazole
2-isopropylaminomethyl-5-(4-chlorophenyl) oxazole
2-methylaminomethyl-5-(4-fluoropuenyl) oxazole
2-ethylaminomethyl-5-(4-fluorophenyl) oxazole
2-aminomethyl-5-(2-chlorophenyl) oxazole
2-methylaminomethyl-5-(3-chlorophenyl) oxazole
2-methylaminomethyl-5-(2-chlorophenyl) oxazole
2-ethylaminomethyl-5-(2-chlorophenyl) oxazole
2-ethylaminomethyl-5-(4-bromophenyl) oxazole
2-ethylaminomethyl-5-(3,4-dichlorophenyl) oxazole
2-propylaminomethyl-5-(4-chlorophenyl) oxazole
2-propylaminomethyl-5-(3-chlorophenyl) oxazole
2-propylaminomethyl-5-(4-fluorophenyl) oxazole
2-diethylaminomethyl-5-(4-chlorophenyl) oxazole
2-[4-(2-hydroxyethyl)-1-piperazinylmethyl]-5-(4-chlorophenyl) oxazole
2-[4-(2-hydroxyethyl)-1-piperazinylmethyl]-5-(3-chlorophenyl) oxazole
2-[4-(2-hydroxyethyl)-1-piperazinylmethyl]-5-(2-chlorophenyl) oxazole
2-[4-(2-hydroxyethyl)-1-piperazinylmethyl]-5-(4-fluorophenyl) oxazole
2-[4-(2-hydroxyethyl)-1-piperazinylmethyl]-5-(4-bromophenyl) oxazole
2-[4-(2-hydroxyethyl)-1-piperazinylmethyl]-5-(3,4-dichlorophenyl) oxazole The pharmaceutically acceptable acid addition salts of the above compounds are, of course, also included within the scope of this invention.

It will be understood that the term "pharmaceutically acceptable acid addition salts" as used herein is intended to include non-toxic salts of the compounds of this invention with an anion.

Representative of such salts are hydrochlorides, hydrobromides, sulfates, phosphates, nitrates, acetates, succinates, adipates, propionates, tartrates, maleates, citrates, benzoates, toluenesulfonates, and methanesulfonates. Of the compounds of this invention, it will be understood that the following compounds are most preferred due to their high level of anti-inflammatory and analgesic activity.

2-methylaminomethyl-5-phenyloxazole
2-ethylaminomethyl-5-(4-chlorophenyl) oxazole
2-[4-(2-hydroxyethyl)-1-piperazinylmethyl]-5-(4-chlorophenyl) oxazole The above compounds are intended only to illustrate the variety of structures which can be used in the process of this invention, and the above listing is not to be construed as limiting the scope of the invention.

For the preparation of the compounds of this invention, various methods can be employed depending upon the particular starting materials and/or intermediates involved.

The 2-aminomethyl-5-phenyloxazole can be prepared by the condensation of a 2-halomethyl-5-phenyloxazole with at least an equimolar amount of a corresponding primary or secondary amine.

The following reaction equation illustrates this method of preparation.

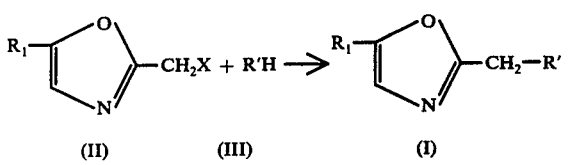

(II)  (III)  (I)

In the above formulas, R₁ and R' are as defined herein above and when R' is

at least one of $R_2$ and $R_3$ is alkyl, and X is halogen.

The condensation reaction is generally effected in a suitable reaction-inert solvent in the presence of a base, such as an organic base (triethylamine, pyridine) or a solution of an inorganic base (sodium hydroxide, sodium carbonate) for a period of from 1 to 30 hours.

The preferred solvents for the condensation includes water, methanol, ethanol, dimethylformamide, tetrahydrofuran and the like. The reaction temperature is not critical, and generally ranges from 0° to 200° C, preferably from 15° to 100° C.

The amount of the primary or secondary amine (III) to be used is generally in the range of 1 to 10 moles per mole of the 2-halomethyl-5-phenyloxazole (II), with from 1 to 3 moles per mole of the 2-halomethyl-5-phenyloxazole (II) being preferred.

After the reaction is complete, the reaction mixture is concentrated to remove the solvent and the excess amine. The residue is partitioned between NaOH solution and chloroform, the chloroform layer separated and dried over a suitable drying agent, and then the solvent is evaporated under reduced pressure. The resulting product (I), after having been converted to the acid addition salt by interaction of the product with an acid in an appropriate medium, e.g., methanol or ethanol, can be recrystallized from a suitable solvent, e.g., methanol or ethanol.

2-Aminomethyl-5-phenyloxazoles wherein $R_2$ and $R_3$ are hydrogen, can be prepared by the reaction of a 2-halomethyl-5-phenyloxazole with potassium phthalimide followed by decomposition of the obtained N-(5-phenyl-2-oxazolyl) methylphthalimide with hydrazine hydrate.

The following reaction equation illustrates this method of preparation.

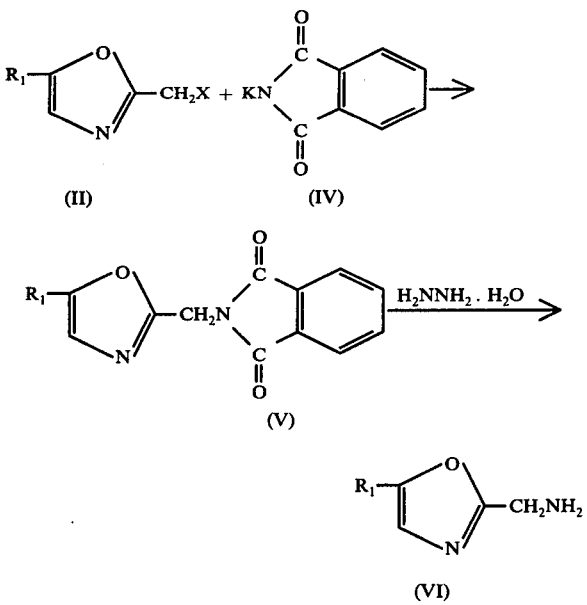

In the above formulas, X is halogen. The reaction between the 2-halomethyl-5-phenyl oxazole (II) and potassium phthalimide (IV) is generally effected in a suitable reaction-inert solvent at a temperature of from 15° to 100° C for a period of from 1 to 30 hours.

The preferred solvents are dimethylformamide and ethanol. The amount of potassium phthalimide to be used is generally in the range of 1 to 10 moles per mole of the 2-halomethyl-5-phenyloxazole (II), with from 1 to 2 moles per mole of the 2-halomethyl-5-phenyloxazole (II) being preferred.

Upon completion of the reaction, the reaction mixture is poured into water to give the precipitate (V) which is filtered and can be purified by recrystallization from a suitable solvent, e.g., ethanol.

The decomposition of the N-(5-phenyl-2-oxazolyl)-methylphthalimide (V) by the action of hydrazine hydrate is generally effected in an alcohol at a temperature of from 15° to 100° C for a period of from 1 to 10 hours.

In general, hydrazine hydrate is used in an amount of 1 to 3 moles per mole of the N-(5-phenyl-2-oxazolyl) methylphthalimide (V).

After the reaction is complete, the formed precipitate is filtered off. The filtrate is evaporated to dryness, and the residue, after having been converted to the acid addition salt, can be purified by recrystallization from a suitable solvent, e.g., ethanol.

The 2-halomethyl-5-phenyloxazoles (II) starting materials can be prepared by the condensation of a phenacylamine with a haloacetyl halide followed by cyclization of the obtained N-phenacylhaloacetamide.

The following reaction equation illustrates this method of preparation.

(VII)

-continued

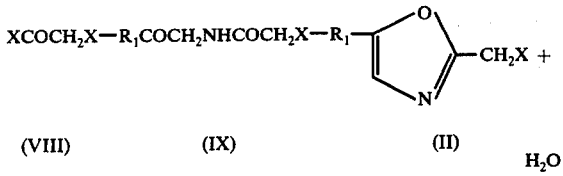

In the above formulas, $R_1$ and X are as defined herein above. The condensation of the phenacylamine (VII) with the haloacetyl halide (VII) is carried out in a suitable solvent, e.g., benzene-water, in the presence of a base, such as sodium hydroxide at a temperature of 0° to 50° C for a period of 1 to 5 hours.

A convenient method of isolation comprises extraction of the product with a water immiscible solvent, e.g., benzene, followed by removal of the solvent. The resultant product can be used in this crude state for the subsequent reaction or can be recrystallized from an appropriate solvent, e.g., ethanol.

The cyclization of the N-phenacylhaloacetamide (IX) to the 2-halomethyl-5-phenyloxazole (II) is carried out in a suitable solvent, e.g., benzene or toluene, in the presence of a dehydrating agent, e.g., phosphorous oxychloride, or sulfuric acid at a temperature of 15° to 100° C for a period of 1 to 5 hours.

The product is conveniently isolated by pouring the reaction mixture into water followed by extraction with a water immiscible solvent such as chloroform. The organic layer is dried over a suitable drying agent and concentrated in vacuo. The isolated product can be used in this crude state or may be further purified by recrystallization.

The 2-aminomethyl-5-phenyloxazoles of this invention form acid addition salts with any of a variety of inorganic and organic acids.

The product of the reactions described above can be isolated in the free form or in the form of an acid addition salt. In addition, the product can be obtained as pharmaceutically acceptable acid addition salts by reacting one of the free bases with an acid.

Likewise, treatment of the salts with a base results in a regeneration of the free base.

Pharmacological testing of the 2-aminomethyl-5-phenyloxazoles has demonstrated that they are useful as anti-inflammatory agents. Analgesic activity has also been found in the compounds of this invention.

The anti-inflammatory activity of the compounds of the present invention was demonstrated in the following test:

The anti-inflammatory activity of the 2-aminomethyl-5-phenyloxazoles was compared with that of aminopyrine.

Eight male rats of Wistar-King strain, each weighing between 120 to 150 grams, were used for each group. The hind paw of the rats was injected subcutaneously with 0.1 ml of 1% carrageenin suspension. The volume of the paw was measured plethysmographically 3 hours after the injection, and the difference in volume between the edematous foot and the normal foot was regarded as the degree of edema. Each percent inhibition was calculated in comparison with the control. The test compounds were administered orally 30 minutes before the injection of carrageenin.

The analgesic activity of the 2-aminomethyl-5-phenyloxazoles was compared with that of aminopyrine.

(A) Writhing syndrome induced by acetic acid

Six male mice of ddY strain, each weighing between 25 to 30 grams were used in the present experiment. The animals were injected intraperitoneally with 0.1 m/10 g of a 0.6% aqueous acetic acid solution 10 minutes after the test compound was injected subcutaneously. Thereafter, the total number of writhings of a group was recorded for 20 minutes, and percent inhibition was calculated in comparison with the control. $ED_{50}$ was calculated according to Litchfield-Wilcoxon's method.

(B) Electrical stimulation method

Five male mice of ddY strain, each weighing between 25 to 30 grams were used for each group. Bipolar electrode was placed on the tail root of mouse. The mouse was stimulated with the square wave (5 m sec, 1 Hz), and the minimum voltage of squeak response was measured at 5, 10, 15, 30, 45 and 60 minutes after intraperitoneal administration of the test compound. Positive analgesic response was determined in cases where increase in the minimum voltage was observed. $ED_{50}$ was calculated according to Weil's method. The actute toxicity values ($LD_{50}$) of the 2-aminoethyl-5-phenyloxazoles were determined in the following manner:

The animals were administered intraperitoneally with the test compounds, and mortality was observed for 168 hours. $LD_{50}$ was calculated according to Weil's method. The results are shown in Table I.

TABLE I

| Compound | Anti-inflammatory Activity (carageenin-induced rat paw inflammation) | | Analgesic Activity | | |
|---|---|---|---|---|---|
| | Oral Dose mg/kg | Percent Inhibition of Swelling | AcOH induced Writhing in Mice $ED_{50}$ (mg/kg. s.c.) | Electrical Stimulation $ED_{50}$ (mg/kg. i.p.) | $LD_{50}$ in Mice (mg/kg. i.p.) |
| ![structure]—CH₂NHCH₃·HCl | 25 | 5 | 10.1 | 32 | 238 |
| | 50 | 40 | | | |
| | 100 | 48 | | | |

TABLE I-continued
| Compound | Anti-inflammatory Activity (carageenin-induced rat paw inflammation) | | Analgesic Activity | | |
|---|---|---|---|---|---|
| | Oral Dose mg/kg | Percent Inhibition of Swelling | AcOH induced Writhing in Mice ED$_{50}$ (mg/kg. s.c.) | Electrical Stimulation ED$_{50}$ (mg/kg. i.p.) | LD$_{50}$ in Mice (mg/kg. i.p.) |
| 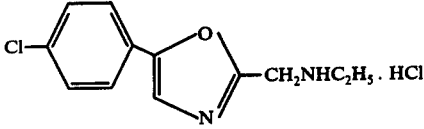 | 12.5<br>25<br>50<br>100 | 16<br>43<br>65<br>60 | 1.9 | 35 | 283 |
| 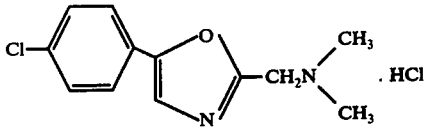 | 100 | 7 | 78 | 77 | 336 |
| 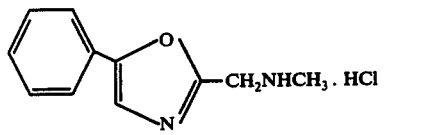 | 25<br>50<br>100 | 5<br>40<br>48 | 10.1 | 32 | 238 |
| 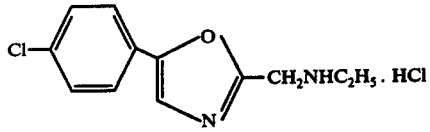 | 12.5<br>25<br>50<br>100 | 16<br>43<br>65<br>60 | 1.9 | 35 | 283 |
| 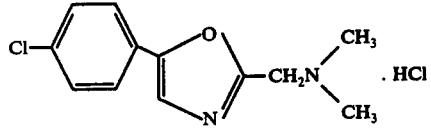 | 100 | 7 | 78 | 77 | 336 |
| 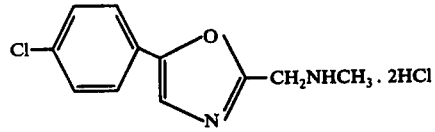 | 100 | 17 | 22 | 46 | 141 |
| 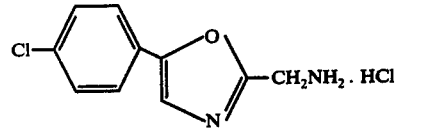 | 25<br>50<br>100 | 25<br>29<br>65 | 6 | 50 | 476 |
| 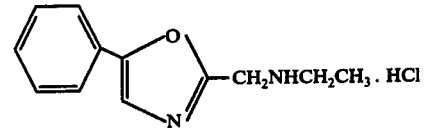 | 50<br>100 | 23<br>47 | | 21.4 | 141 |
| 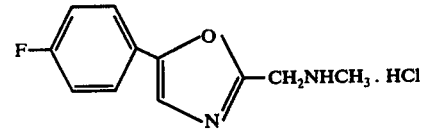 | 50<br>100 | 38<br>55 | | | 141 |

TABLE I-continued
| Compound | Anti-inflammatory Activity (carageenin-induced rat paw inflammation) | | Analgesic Activity | | LD$_{50}$ in Mice (mg/kg. i.p.) |
|---|---|---|---|---|---|
| | Oral Dose mg/kg | Percent Inhibition of Swelling | AcOH induced Writhing in Mice ED$_{50}$ (mg/kg. s.c.) | Electrical Stimulation ED$_{50}$ (mg/kg. i.p.) | |
| 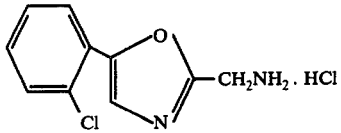 | 25<br>50<br>100 | 28<br>58<br>42 | | | 283 |
| 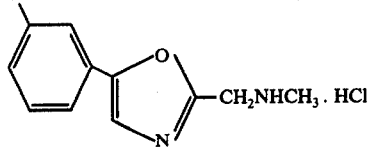 | 100 | 21 | | | 283 |
| 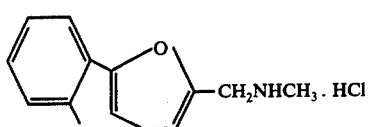 | 100 | 14 | | | 141 |
| 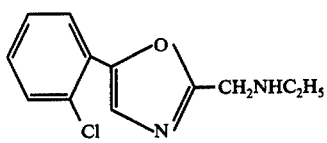 | 100 | 14 | | 54 | 141 |
| 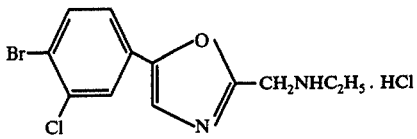 | 100 | 22 | | | 168 |
| 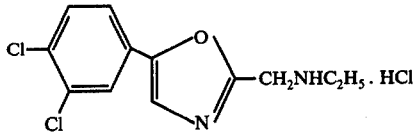 | 25<br>50<br>100 | 27<br>56<br>68 | | | 141 |
| 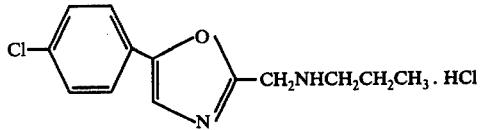 | 50<br>100 | 24<br>38 | | 47 | 566 |
| 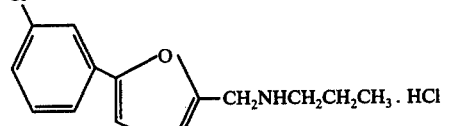 | 50<br>100 | 4<br>32 | | | 283 |
| 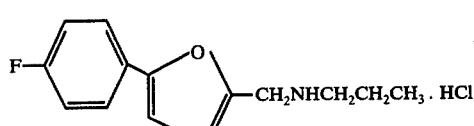 | 50<br>100 | 45<br>53 | | 54 | 238 |

TABLE I-continued

| Compound | Anti-inflammatory Activity (carageenin-induced rat paw inflammation) | | Analgesic Activity | | $LD_{50}$ in Mice (mg/kg. i.p.) |
|---|---|---|---|---|---|
| | Oral Dose mg/kg | Percent Inhibition of Swelling | AcOH induced Writhing in Mice $ED_{50}$ (mg/kg. s.c.) | Electrical Stimulation $ED_{50}$ (mg/kg. i.p.) | |
| Cl—C₆H₄—oxazole—CH₂N(C₂H₅)₂ · HCl · ½H₂O | 50<br>100 | 24<br>44 | | | 238 |
| Cl,Cl—C₆H₃—oxazole—CH₂—N(piperazine)N—CH₂CH₂OH · 2HCl | 100 | 14 | | | 141 |
| C₆H₅—oxazole—CH₂—N(piperazine)N—CH₂CH₂OH · 2HCl | 100 | 6 | | | 283 |
| F—C₆H₄—oxazole—CH₂—N(piperazine)N—CH₂CH₂OH · 2HCl | 50<br>100 | 8<br>54 | | | 336 |
| Cl—C₆H₄—oxazole—CH₂—N(piperazine)N—CH₂CH₂OH · 2HCl | 12.5<br>25<br>50<br>100 | 6<br>27<br>57<br>50 | 16.0 | 30.8 | 283 |
| Aminopyrine | 12.5<br>25<br>50<br>100 | 9<br>23<br>47<br>65 | 37 | 96 | 270 |

The therapeutic agents of this invention may be administered alone or in combination with pharmaceutically acceptable carriers, the proportion of which is determined by the solubility and chemical nature of the compound, chosen route of administration and standard pharmaceutical practice. For example, the compounds may be injected parenterally, that is, intramuscularly, intravenously or subcutaneously. For parenteral administration, the compounds may be used in the form of sterile solutions containing other solutes, for example, sufficient saline or glucose to make the solution isotonic. The compounds may be administered orally in the form of tablets, capsules, or granules containing suitable excipients such as starch, lactose, white sugar and the like. The compounds may be administered sublingually in the form of troches or lozenges in which each active ingredient is mixed with sugar or corn syrups, flavoring agents and dyes, and then dehydrated sufficiently to make the mixture suitable for pressing into solid form. The compounds may be administered orally in the form of solutions which may contain coloring and flavoring agents.

Physicians will determine the dosage of the present therapeutic agents which will be most suitable, and dosages vary with the mode of administration and the particular compound chosen. In addition, the dosage will vary with the particular patient under treatment.

When the composition is administered orally, a larger quantity of the active agent will be required to produce the same effect as caused with a smaller quantity given parenterally. The therapeutic dosage is generally 10–50 mg/kg of active ingredient parenterally, 50–300 mg/kg orally per day.

Having generally described the invention, a more complete understanding can be obtained by reference to certain specific examples, which are included for purposes of illustration only and are not intended to be limiting unless otherwise specified.

EXAMPLE 1

(A) N-(4-chlorophenacyl) chloroacetamide

To a well stirred suspension of 20.6 g of 4-chlorophenacylamine hydrochloride in 70 ml of benzene and 70 ml of water which was cooled to below 7° C were added simultaneously 110 ml of 2N NaOH solution and 12.4 g of chloroacetyl chloride dissolved in 30 ml of benzene. After the addition was complete, the reaction mixture was warmed to room temperature and stirred at room temperature for 3 hours. At the end of this period, the formed precipitate was filtered, and the benzene layer was separated. The aqueous layer was extracted twice with 50 ml of benzene. The combined benzene layer was dried over anhydrous sodium sulfate, and evaporated to dryness. The residue together with the precipitate obtained above was combined and recrystallized from ethanol to give 14.1 g (57 percent) of N-(4-chlorophenacyl) chloroacetamide.

(B) 2-Chloromethyl-5-(4-chlorophenyl)oxazole

A suspension of 12.3 g of N-(chlorophenacyl) chloroacetamide and 19.2 g of phosphorous oxychloride in 100 ml of benzene was heated at reflux for 2.5 hours. At the end of this period, the excess phosphorous oxychloride was removed in vacuo. The residue was poured into 200 ml of water and extracted with 100 ml of chloroform. The aqueous layer was extracted twice with 40 ml of chloroform.

The combined chloroform layer was dried over anhydrous sodium sulfate and evaporated under reduced pressure to give 10.7 g (94%) of crude 2-chloromethyl-5-(4-chlorophenyl) oxazole. Recrystallization from aqueous ethanol gave pure 2-chloromethyl-5-(4-chlorophenyl) oxazole, M.P. 50°-60° C.

(C) 2-Ethylaminomethyl-5-(4-chlorophenyl) oxazole hydrochloride

To a solution of 2.3 g of 2-chloromethyl-5-(4-chlorophenyl) oxazole in 50 ml of ethanol was added 3.2 g of 70% ethylamine aqueous solution, and the resultant solution was allowed to stand at room temperature overnight. At the end of this time, the solvent and the excess ethylamine were distilled off under reduced pressure, and then 30 ml of water, 10 ml of 2N NaOH solution and 50 ml of chloroform were added. The chloroform layer was separated and the aqueous layer was extracted twice with 30 ml of chloroform. The combined chloroform layer was dried over anhydrous sodium sulfate, and the solvent was removed in vacuo to give 2.1 g of crude 2-ethylaminomethyl-5-(4-chlorophenyl) oxazole. This was dissolved in 15 ml of ethanol, and 5 ml of ethanolic saturated hydrogen chloride solution was added. Evaporation of the solvent followed by recrystallization from ethanol afforded 2.0 g (73 percent) of 2-ethylaminomethyl-5-(4-chlorophenyl) oxazole hydrochloride, M. P. 194°-6° C.

I.R. (KBr): 2,950, 2,740, 1,480, 1,450, 1,115 1,090 810 $cm^{-1}$. N.M.R. ($CDCl_3$, free base): $\delta$ 1.13 (triplet, $-NCH_2CH_3$), 1.77 (singlet, $-NH-$), 2.72 (quartet, $-NCH_2CH_3$), 3.90 (singlet $-CH_2N-$), 7.15

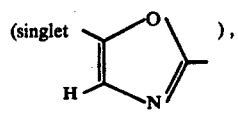

7.34

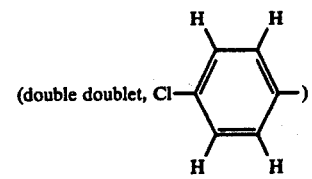

p.p.m.

Analysis - Calcd. for $C_{12}H_{13}N_2O_1Cl_1 \cdot HCl$ (percent): C, 52.76; H, 5.17; N, 10.26; Cl, 25.96. Found (percent): C, 52.73; H, 5.09; N, 10.25; Cl, 25.71.

Various other 2-aminomethyl-5-phenyloxazoles were synthesized in accordance with the procedure of Example 1, and the results are summarized in Table II.

TABLE II

| | | | | | Elemental analysis Upper: Calculated (percent) Lower: Found (percent) | | | |
|---|---|---|---|---|---|---|---|---|
| No. | $R_1$ | $-N\begin{matrix}R_2\\R_3\end{matrix}$ | Addition moiety | M. P. (° C) | Yield (%) | C | H | N | Cl |
| 1 | phenyl | $-NHCH_3$ | HCl | 186–188 | 79 | 58.80 58.72 | 5.83 5.90 | 12.47 12.26 | 15.78 15.69 |
| 2 | phenyl | $-NHCH_2CH_3$ | HCl | 166–168 | 76 | 60.37 60.19 | 6.33 6.36 | 11.74 11.68 | 14.85 14.75 |
| 3 | phenyl | $-NHCH_2CH_2CH_3$ | HCl | 194–196 | 82 | 61.77 61.74 | 6.78 6.87 | 11.09 11.18 | 14.03 13.81 |
| 4 | phenyl | $-NHCH(CH_3)_2$ | HCl | 197–198 | 85 | 53.99 54.05 | 6.27 6.24 | 9.69 9.74 | 24.52 24.36 |

TABLE II-continued

| # | Aryl | R | Salt | mp (°C) | Yield % | C (calc/found) | H (calc/found) | N (calc/found) | X (calc/found) |
|---|---|---|---|---|---|---|---|---|---|
| 5 | phenyl | —NH(CH$_2$)$_3$CH$_3$ | HCl | 150–152 | 75 | 63.03 / 63.08 | 7.17 / 7.23 | 10.50 / 10.49 | 13.29 / 13.21 |
| 6 | phenyl | —N(CH$_3$)$_2$ | HCl | 179–181 | 88 | 60.37 / 60.30 | 6.33 / 6.41 | 11.74 / 11.56 | 14.85 / 14.83 |
| 7 | 4-Cl-phenyl | —NHCH$_3$ | 2HCl | 159–162 | 77 | 44.70 / 45.00 | 4.43 / 4.38 | 9.48 / 9.64 | 35.98 / 35.58 |
| 8 | 4-Cl-phenyl | —NHCH(CH$_3$)$_2$ | 2HCl | 215–217 | 83 | 54.36 / 54.31 | 5.62 / 5.62 | 9.76 / 9.79 | 24.69 / 24.37 |
| 9 | 4-Cl-phenyl | —N(CH$_3$)$_2$ | HCl | 180–182 | 90 | 52.76 / 52.41 | 5.17 / 5.11 | 10.25 / 10.34 | 25.96 / 25.90 |
| 10 | 4-F-phenyl | —NHCH$_3$ | HCl | 160–161 | 78 | 47.32 / 47.20 | 4.69 / 4.64 | 10.03 / 9.99 | 25.40 / 24.90 |
| 11 | 4-F-phenyl | —NHCH$_2$CH$_3$ | HCl | 165–166 | 80 | 56.14 / 56.20 | 5.50 / 5.44 | 10.92 / 10.68 | |
| 12 | 3-Cl-phenyl | —NHCH$_3$ | HCl | 188–193 | 83 | 50.98 / 50.74 | 4.67 / 4.73 | 10.81 / 10.71 | 27.36 / 27.16 |
| 13 | 2-Cl-phenyl | —NHCH$_3$ | HCl | 201–203 | 85 | 50.98 / 50.80 | 4.67 / 4.60 | 10.81 / 10.61 | 27.36 / 27.20 |
| 14 | 2-Cl-phenyl | —NHC$_2$H$_5$ | | 193–196 | 78 | 52.76 / 52.96 | 5.17 / 5.07 | 10.26 / 10.20 | 25.96 / 25.90 |
| 15 | 4-Br-phenyl | —NHC$_2$H$_5$ | HCl | 206–209 | 75 | 45.38 / 45.20 | 4.44 / 4.40 | 8.82 / 8.80 | |
| 16 | 3,4-diCl-phenyl | —NHC$_2$H$_5$ | HCl | 195–199 | 85 | 46.86 / 46.88 | 4.26 / 4.26 | 9.11 / 9.05 | 34.58 / 34.44 |
| 17 | 4-Cl-phenyl | —NHCH$_2$CH$_2$CH$_3$ | HCl | 235–240 | 84 | 54.37 / 54.11 | 5.62 / 5.45 | 9.75 / 9.53 | 24.69 / 24.58 |

TABLE II-continued

| No. | R₁ | Addition moiety | | M.P. (°C) | Yield (%) | C | H | N | Cl |
|---|---|---|---|---|---|---|---|---|---|
| 18 | 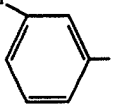 3-Cl-C₆H₄ | —NHCH₂CH₂CH₃ | HCl | 199–201 | 78 | 54.37 54.20 | 5.62 5.50 | 9.75 9.70 | 24.69 24.60 |
| 19 | 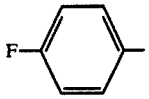 4-F-C₆H₄ | —NHCH₂CH₂CH₃ | HCl | 183–185 | 80 | 57.67 57.60 | 5.96 5.94 | 10.35 10.18 | |
| 20 | 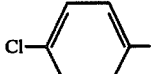 4-Cl-C₆H₄ | —N(C₂H₅)₂ | HCl · ½ H₂O | 124–126 | 75 | 54.20 54.47 | 6.17 6.05 | 9.03 8.98 | 22.85 23.03 |
| 21 | 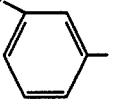 3-Cl-C₆H₄ | —NHCH₂CH₃ | HCl | 219–221 | 70 | 52.76 52.96 | 5.17 5.07 | 10.26 10.20 | |

Compound

R₁—[oxazole]—CH₂—N(piperazine)N—CH₂CH₂OH

| No. | R₁ | Addition moiety | M.P. (°C) | Yield (%) | C | H | N | Cl |
|---|---|---|---|---|---|---|---|---|
| 21 | 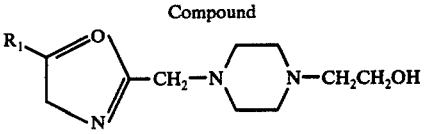 | 2HCl | 190–195 | 69 | 53.34 53.28 | 6.43 6.36 | 11.66 11.65 | 19.68 19.63 |
| 22 | 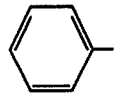 | 2HCl | 196–202 | 71 | 50.80 50.58 | 5.86 5.87 | 11.11 11.06 | 18.74 18.82 |
| 23 | 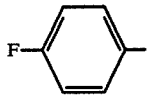 | 2HCl | 195–198 | 73 | 48.68 48.59 | 5.62 5.55 | 10.65 10.65 | |
| 24 | 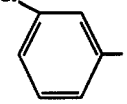 | 2HCl | 185–190 | 68 | 48.68 48.38 | 5.62 5.60 | 10.65 10.62 | 26.95 26.73 |
| 25 | 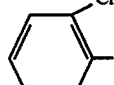 | 2HCl | 195–200 | 72 | 43.76 43.94 | 5.05 4.93 | 9.57 9.61 | |
| 26 | 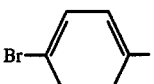 | 2HCl | 218–223 | 74 | 44.78 44.68 | 4.93 5.01 | 9.79 9.61 | 33.04 32.93 |

The following compounds are prepared in a similar manner.

2-butylaminomethyl-5-(4-chlorophenyl) oxazole
2-sec-butylaminomethyl-5-(4-chlorophenyl) oxazole
2-isobutylaminomethyl-5-(4-chlorophenyl) oxazole
2-octylaminomethyl-5-(4-chlorophenyl) oxazole
2-ethylaminomethyl-5-(3-chlorophenyl) oxazole
2-propylaminomethyl-5-(2-chlorophenyl) oxazole
2-methylaminomethyl-5-(4-bromophenyl) oxazole
2-methylaminomethyl-5-(3-bromophenyl) oxazole
2-methylaminomethyl-5-(2-bromophenyl) oxazole
2-ethylaminomethyl-5-(3-bromophenyl) oxazole
2-ethylaminomethyl-5-(2-bromophenyl) oxazole
2-propylaminomethyl-5-(4-bromophenyl) oxazole
2-propylaminomethyl-5-(3-bromophenyl) oxazole
2-propylaminomethyl-5-(2-bromophenyl) oxazole
2-methylaminomethyl-5-(4-fluorophenyl) oxazole
2-methylaminomethyl-5-(3-fluorophenyl) oxazole 2-methylaminomethyl-5-(2-fluorophenyl) oxazole
2-ethylaminomethyl-5-(4-fluorophenyl) oxazole
2-ethylaminomethyl-5-(3-fluorophenyl) oxazole
2-ethylaminomethyl-5-(2-fluorophenyl) oxazole
2-propylaminomethyl-5-(3-fluorophenyl) oxazole
2-propylaminomethyl-5-(2-fluorophenyl) oxazole 2-diethylaminomethyl-5-(4-chlorophenyl) oxazole
2-[4-(2-hydroxyethyl)piperazinylmethyl]-5-(2-fluorophenyl) oxazole
2-[4-(2-hydroxyethyl)piperazinylmethyl]-5-(3-fluorophenyl) oxazole
2-[4-(2-hydroxyethyl)piperazinylmethyl]-5-(2-bromophenyl) oxazole
2-[4-(2-hydroxyethyl)piperazinylmethyl]-5-(3-bromophenyl) oxazole
2-[4-(2-hydroxyethyl)piperazinylmethyl]-5-(4-iodophenyl) oxazole

EXAMPLE 2

(A)

N-[5-(4-chlorophenyl)-2-oxazolyl]methylphthalimide

A suspension of 2.3 g of 2-chloromethyl-5-(4-chlorophenyl) oxazole and 1.94 g of potassium phthalimide in 15 ml of dimethylformamide was stirred at room temperature for one hour. The reaction mixture was poured into 300 ml of water, and the resultant precipitate was filtered and recrystallized from ethanol to give 2.4 g (71 percent) of N-[5-(4-chlorophenyl)-2-oxazolyl]methylphthalimide.

(B) 2-aminomethyl-5-(4-chlorophenyl) oxazole hydrochloride

A solution of 3.4 g of N-[5-(4-chlorophenyl)-2-oxazolyl]methylphthalimide and 0.55 g of 100% hydrazine hydrate in 50 ml of ethanol was heated at reflux for one hour. At the end of this period, the formed precipitate was filtered off, and the filtrate was evaporated to dryness in vacuo. The residue was shaken with 2N HCl - chloroform and the 2N HCl - layer was evaporated to dryness under vacuo. The residue was recrystallized from ethanol to give 1.9 g (78 percent) of 2-aminomethyl-5-(4-chlorophenyl) oxazole hydrochloride, M.P. 200° C (decomposition).

I.R. (KBr, free base): 3,340 1,550 1,480 1,100 940 820 cm$^{-1}$. N.M.R. (CDCl$_3$, free base): δ 4.50 (singlet, >—CH$_2$N<), 7.70 (singlet, oxazole ring), 7.73 (double doublet, 4-chlorophenyl) p.p.m.

Analysis - Calcd. for C$_{10}$H$_{10}$ON$_2$.HCl (percent): C, 49.00; H, 4.11; N, 11.43; Cl, 28.93. Found (percent): C, 48.79; H, 4.20; N, 11.18; Cl, 29.06.

Various other 2-aminomethyl-5-phenyloxazoles were synthesized in accordance with the procedure of Example 2, and the results are summarized in Table III.

TABLE III

| No. | R$_1$ | Addition moiety | M.P. (°C) | Yield (%) | Elemental Analysis Upper: Calculated (percent) Lower: Found (percent) | | | |
|---|---|---|---|---|---|---|---|---|
| | | | | | C | H | N | Cl |
| 1 | phenyl | HCl | 232–236 | 81 | 57.01 | 5.26 | 13.30 | 16.83 |
| | | | | | 56.69 | 5.26 | 13.28 | 17.18 |
| 2 | 4-fluorophenyl | HCl | 233–237 | 78 | 52.52 | 4.41 | 12.25 | |
| | | | | | 52.38 | 4.41 | 12.05 | |
| 3 | 2-chlorophenyl | HCl | 194–199 | 79 | 49.00 | 4.11 | 11.43 | 28.93 |
| | | | | | 49.10 | 4.11 | 11.40 | 28.83 |

The following compounds are prepared in a similar manner.

2-aminomethyl-5-(3-chlorophenyl) oxazole
2-aminomethyl-5-(4-bromophenyl) oxazole
2-aminomethyl-5-(3-bromophenyl) oxazole
2-aminomethyl-5-(2-bromophenyl) oxazole
2-aminomethyl-5-(4-fluorophenyl) oxazole
2-aminomethyl-5-(3-fluorophenyl) oxazole
2-aminomethyl-5-(2-fluorophenyl) oxazole

EXAMPLE 3

Tablets suitable for oral administration

Tablets containing the ingredients indicated below may be prepared by conventional techniques.

| Ingredient | Amount per tablet (mg) |
| --- | --- |
| 5-(4-chlorophenyl)-2-ethylaminomethyloxazole hydrochloride | 125 |
| Lactose | 30 |
| Corn starch | 20 |
| Crystalline cellulose | 75 |
| Silica | 2 |
| Magnesium stearate | 2 |
| Total | 254 mg |

EXAMPLE 4

Capsules for oral administration

Capsules of the below were made up by thoroughly mixing together batches of the ingredients and filling hard gelatin capsules with the mixture.

| Ingredient | Amount per capsule (mg) |
| --- | --- |
| 5-(4-chlorophenyl)-2-ethylaminomethyloxazole hydrochloride | 250 |
| Magnesium stearate | 2 |
| Lactose | 48 |
| Total | 300 mg |

EXAMPLE 5

Sterile solution for infusion

A 0.25 g portion of 5-(4-chlorophenyl)-2-ethylaminomethyloxazole hydrochloride is dissolved in saline to give a total volume of 500 ml and the resulting solution is then sterilized.

What is claimed as new and intended to be covered by Letters Patent is:

1. A 2-aminomethyl-5-phenyloxazole having the formula (I):

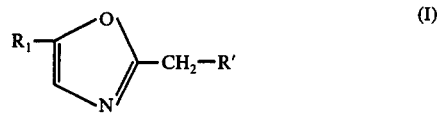

wherein $R_1$ is phenyl or halophenyl; $R'$ is 4-(2-hydroxyethyl)-1-piperazinyl or the pharmaceutically acceptable acid addition salts thereof.

2. The compound of claim 1, wherein $R_1$ is selected from the group consisting of phenyl, 2-chlorophenyl, 3-chlorophenyl, 4-chlorophenyl, 3,4-dichlorophenyl, 2-fluorophenyl, 3-fluorophenyl, 4-fluorophenyl, 2-bromophenyl, 3-bromophenyl, 4-bromophenyl and 4-iodophenyl; $R'$ is 4-(2-hydroxyethyl)-1-piperazinyl.

3. The compound of claim 2, wherein $R_1$ is selected from the group consisting of phenyl, 2-chlorophenyl, 3-chlorophenyl, 4-chlorophenyl, 4-fluorophenyl and 4-bromophenyl; and $R'$ is 4-(2-hydroxyethyl)-1-piperazinyl.

4. A method of meliorating inflammation in warm blooded animals, which comprises administering to said animal an anti-inflammatory effective amount of a compound having the formula (I):

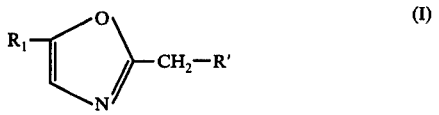

wherein $R_1$ is phenyl or halophenyl; $R'$ is 4-(2-hydroxyethyl)-1-piperazinyl.

5. A compound of claim 3, which is 2-[4-(2-hydroxyethyl)-1-piperazinylmethyl]-5-(4-chlorophenyl) oxazole.

* * * * *